United States Patent
Stamler et al.

(10) Patent No.: US 8,664,269 B2
(45) Date of Patent: Mar. 4, 2014

(54) NITROGLYCERIN THERAPY FOR THOSE UNABLE TO METABOLIZE NITROGLYCERIN

(75) Inventors: Jonathan S. Stamler, Chapel Hill, NC (US); Gregory T. Went, Mill Valley, CA (US)

(73) Assignee: Duke University, Durham, NC (US)

( * ) Notice: Subject to any disclaimer, the term of this patent is extended or adjusted under 35 U.S.C. 154(b) by 1630 days.

(21) Appl. No.: 11/594,214

(22) Filed: Nov. 8, 2006

(65) Prior Publication Data

US 2007/0123585 A1    May 31, 2007

Related U.S. Application Data

(60) Provisional application No. 60/740,267, filed on Nov. 29, 2005.

(51) Int. Cl.
 *A61K 31/21*    (2006.01)
 *A61K 31/195*    (2006.01)

(52) U.S. Cl.
 USPC .......................................... 514/509; 514/562

(58) Field of Classification Search
 USPC ................................. 514/509, 562
 See application file for complete search history.

(56) References Cited

U.S. PATENT DOCUMENTS

| | | |
|---|---|---|
| 2004/0014721 A1 | 1/2004 | Hensley et al. |
| 2005/0131063 A1 | 6/2005 | Stamler et al. |
| 2005/0148612 A1 | 7/2005 | Stamler et al. |

OTHER PUBLICATIONS

Chen, Zhiciiang, et al., "An essential role for mitochondrial aldehyde dehydrogenase in nitroglycerin bioactivation", PNAS, vol. 102, No. 34, Aug. 23, 2005, pp. 12159-12164.
Chen, Z., et al., "Identification of the Enzymatic Mechanism of Nitroglycerin Bioactivation", PNAS, vol. 99, No. 12, Jun. 11, 2002, and as published online before print on Jun. 4, 2002, at www.pnas.org/cgi/doi/10.1073/pnas.122225199, p. 8306-8311.
Fink, D.S., et al., "Comparison of Glyceryl Trinitrate-Induced With Pentaerythrityl Tetranitrate-Induced in Vivo Formation of Superoxide Radicals: Effect of Vitamin C", Abstract, NCBI, PubMed, Jul. 27, 1999 (1-2):170-6, 2 pages.
Dikalov, S., et al., "Formation of Reactive Oxygen Species by Pentaerithrityltetranitrate and Glyceryl Trinitrate in Vitro and Development of Nitrate Tolerance", The Journal of Pharmacology and Expreimental Therapeutics, vol. 286, No. 2, 1998, pp. 938-943.
Fink, B., et al., "Association Between Vascular Tolerance and Platelet Upregulation: Comparison of Nonintermittent Administration of Pentaerithrityltetranitrate and Glyceryltrinitrate", Abstract, NCBI, PubMed, Dec. 2002; 40(6):890-7, 2 pages.
Fink, B., et al., "Unexpected, Tolerance-Devoid Vasomotor and Platelet Actions of Pentaerythrityl Tetranitrate", Journal of Cardiovascular Pharmacology, 30(6):831-836, Dec. 1997—Abstract, 1 page.
Horowitz, J.D., et al., "Potentiation of the Cardiovascular Effects of Nitroglycerin by N-acetylcysteine", Circulation, vol. 68, pp. 1247-1253, Copyright © 1983 by American Heart Association—Abstract, 3 pages.
Mackenzie, I.S., et al., "Aldehyde Dehydrogenase 2 Plays a Role in the Bioactivation of Nitroglycerin in Humans", Arteriosclerosis, Thrombosis, and Vascular Biology, Sep. 2005; 25:1891-1895, as published online before print on Jul. 28, 2005. 2 pages.
Kearney, M.F., et al., "Thiol Agents Separate Nitric Oxide Formation from Vasodilation Induced by Glyceryl Trinitrate", Drug Metabolism and Disposition, vol. 26, Issue 6, pp. 547-551, Jun. 1998, printed online version, 12 pages.
McVeigh, G.E., et al., "Platelet Nitric Oxide and Superoxide Release During the Development of Nitrate Tolerance", Circulation, 2002;106:208 © 2002 by American Heart Association, Inc., as published online before print on Jun. 17, 2002, 15 pages.
Metelitsa, VI, M.S., et al., "Relation of the Anti-anginal Effect of Nitroglycerin and its Blood Level in Patients With Stable Exertion-induced Stenocardia", NCBI, PubMed, Kardiologiia, Oct. 1998; 28(10):10-4, 1 page.
Ene-Choo, T., et al., "Heterozygosities and Allelic Frequencies of a Set of Microsatellite Markers Used for Genome-wide Scans in a Chinese Population", PubMed, J. Med. Microbiol. Jan. 2002; 51:76-82, Abstract, 1 page.
Wheatley, R.M., et al., "Interactions of Nitroglycerin and Sulfhydryl-donating Compounds in Coronary Microvessels", The American Physiological Society. 1994, H291-H297.
Winniford, M.D., et al., "Potentiation of Nitrogylcerin-induced Coronary Dilation by N-acetylcysteine", Circulation, vol. 73, 138-142, Copyright © 1986 by American Heart Association, 3 pages.

*Primary Examiner* — Kevin E Weddington
(74) *Attorney, Agent, or Firm* — Bacon & Thomas, PLLC

(57) ABSTRACT

Those in need of nitroglycerin (GTN) therapy who have polymorphism in the mtALDH gene, e.g., those of Asian descent for whom this polymorphism is common, and/or who are being treated with or ingesting or exposed to mtALDH inhibitor are treated with GTN in combination with agent which converts GTN to product which is metabolized without mtALDH activity, e.g., N-acetylcysteine.

15 Claims, No Drawings

NITROGLYCERIN THERAPY FOR THOSE UNABLE TO METABOLIZE NITROGLYCERIN

CROSS-REFERENCE TO RELATED APPLICATION

This application claims the benefit of U.S. Provisional Patent Application No. 60/740,267, filed Nov. 29, 2005.

TECHNICAL FIELD

The invention is directed to a method of treating those in need of nitroglycerin (GTN) therapy.

BACKGROUND OF THE INVENTION

For over 130 years GTN has been used to treat angina and heart failure. However, the mechanism of GTN biotransformation has remained a mystery, and it has not been well understood why tolerance (GTN loss of clinical efficacy) develops over time.

Only recently has a mechanism for GTN biotransformation been identified. More particularly, it has been discovered that the mechanism of biotransformation of nitroglycerin is that the enzyme mitochondrial aldehyde dehydrogenase (mtALDH) catalyzes the formation of 1,2-glyceryl dinitrate and 1,2-glyceryl dinitrite therefrom, leading to production of cGMP and vascular smooth muscle relaxation and that tolerance to GTN is developed as a result of mtALDH inactivation. See Chen, Z., Zhang, J., and Stamler, J. S., Proc. Natl. Acad. Sci. USA 99 (12) 8306-8311 (published on-line Jun. 4, 2002). The above explains why those with a polymorphism in the mtALDH gene and those being treated with or ingesting or exposed to mtALDH inhibitors, are resistant to GTN therapy. The polymorphism effect is important because approximately 20% of those of Chinese descent and approximately 50% of those of Japanese descent have a polymorphism in the mtALDH gene that greatly attenuates their response to nitroglycerin. In other words, a major percentage of those of East Asian descent have not been able to benefit from actions of GTN. The mtALDH inhibitor effect is important because several common treating agents, alcoholic beverages and at least one food are mtALDH inhibitors, including acetaminophen, chloral hydrate, cyanamide, diadzin, sulfonylurea (insulin), sulfiram, ethanol and soy.

Intravenous N-acetyl cysteine (NAC), in short term studies on patients receiving continuous GTN, has been reported to reverse GTN tolerance. See Ghio, S., et al., Circulation 86: 798-802 (1992) and May, D. C., et al., N. Engl. J. Med. 317, 805-809 (1987). However, the mechanism of how this reversal may be effected has not been reported nor has NAC been recognized as a means to enable benefit from GTN therapy in those with polymorphism in the mtALDH gene or being treated with or ingesting or exposed to mtALDH inhibitors.

SUMMARY OF THE INVENTION

It has now been discovered that patients in need of GTN therapy who have attenuated response to GTN therapy are no longer resistant to GTN therapy if concurrently treated with agent which converts GTN to product which is metabolized without mtALDH activity.

In one embodiment herein, denoted the first embodiment herein, the invention is directed to a method of treating a patient in need of GTN therapy where there is a loss-of-function in the patient's mtALDH gene because of polymorphism in the gene, comprising administering to that patient a therapeutically effective amount of GTN and a therapeutically effective amount of agent which converts GTN to thionitrate ($RSNO_2$) and/or thionitrite (RSNO) and/or related nitric oxide congener which is metabolized without mtALDH activity.

In another embodiment herein, denoted the second embodiment herein, the invention is directed to a method of treating a patient of East Asian descent, e.g., of Chinese or Japanese descent, who has attenuated response to GTN therapy, comprising administering to that patient a therapeutically effective amount of agent which converts GTN to thionitrate and/or thionitrite which is metabolized without mtALDH activity. East Asian descent can be determined by facial characteristics or by answers to a questionnaire. Chinese descent can also be determined by microsatellite markers as described in J. Med. Microbiol. 51, 76-82 (January 2005).

In another embodiment herein, denoted the third embodiment herein, the invention is directed to a method of treating a patient in need of GTN therapy who is resistant to GTN therapy because of treatment with or ingestion of or exposure to a mtALDH inhibitor, comprising administering to that patient a therapeutically effective amount of GTN and a therapeutically effective amount of agent which converts GTN to thionitrate and/or thionitrite, which is metabolized without mtALDH activity.

In another embodiment herein, denoted the fourth embodiment herein, the invention is directed to treating a patient who is in need of GTN therapy who is an alcoholic and is addicted to and therefore needs to ingest ethanol and/or who wants to consume ethanol, comprising administering to that patient a therapeutically effective amount of GTN and a therapeutically effective amount of agent which converts GTN to thionitrate and/or thionitrite which is metabolized without mtALDH activity.

In yet another embodiment herein, denoted the fifth embodiment herein, the invention is directed to composition for use in any of the first four embodiments.

The term "patient in need of GTN therapy" is used herein to mean a patient in need of vascular smooth muscle relaxation.

mtALDH referred to in the disclosure of the invention hereinafter is human mtALDH (also known as ALDH2) and is a known enzyme and is described in Vasiton, V., Chemico-Biological Internations 129, 1-19 (2000). The mtALDH gene referred to herein is the human gene that expresses said enzyme.

The term "loss-of-function in the patient's mtALDH activity means attenuated ability to convert GTN to 1,2-glyceryl dinitrate and 1,2-glyceryl dinitrite.

The term "polymorphism" is used herein to mean mutation in the mtALDH gene so that the protein it expresses has attenuated function to convert GTN to thionitrate and/or thionitrite and/or nitrite or nitric oxide.

The term "therapeutically effective amount of GTN" is used herein to mean a sufficient amount to provide sufficient thionitrate and/or thionitrite on conversion by agent described, for metabolizing to nitric oxide and/or nitric oxide congener to effect vascular smooth muscle relaxation and or to relieve patient symptoms.

The term "therapeutically effective amount of agent which converts GTN to thionitrate and/or thionitrite" means amount sufficient to convert the therapeutically effective amount of GTN to sufficient thionitrate and/or thionitrite for metabolizing to nitric oxide and/or nitric oxide congener to effect vascular smooth muscle relaxation.

The term "convert GTN to thionitrate and/or thionitrite which is metabolized without mtALDH activity" means metabolized in the body to nitric oxide and/or nitric oxide congener which effects vascular smooth muscle relaxation.

The term "attenuated response to GTN therapy" means insufficient response to effect vascular smooth muscle relaxation in sufficient degree to ameliorate precordial discomfort and pressure and/or to reduce pulmonary congestion or blood pressure and/or increase ventricular function, from pathogical levels.

The term "mtALDH inhibitor" is used herein to mean compound or composition that interferes with the mtALDH function by competitive or non-competitive inhibition.

Turning now to explanation of the fourth embodiment. The human body relies on wild type mtALDH to detoxify ethanol and metabolites thereof. Thus ethanol acts as a competitive inhibitor of mtALDH's ability to convert GTN to 1,2-glyceryl dinitrate and 1,2-glyceryl dinitrite.

DETAILED DESCRIPTION

The patient in need of GTN therapy includes a patient with an unstable coronary syndrome including angina, myocardial infarction, restenosis, heart failure, hypertension, obstructive, inflammatory or interstitial lung disease, rectal spasm or stroke.

The GTN administration for all embodiments herein is the dosage conventionally used for the disorder that is being treated, e.g., an amount effective to reduce precordial discomfort and pressure for treating a patient with angina, and an amount effective to reduce pulmonary congestion and increase ventricular function, for treating a patient's congestive heart disease.

Typically dosage ranges from 1 mcg/min to 1000 mcg/min IV, sublingually at 0.3 to 0.6 mg for acute relief and in an ointment (2%) over 0.5 to 3 inches (15 mg per inch) over 6 hours, for angina; and sublingual GTN 0.4 mg repeated in 5 minutes followed by IV GTN at 10 to 100 mg/min, for congestive heart failure. GTN can also be administered orally in a sustained release tablet, spray or capsule at 1 to 10 mg or can be nebulized.

The GTN converting agent for all embodiments is a thiol of molecular mass less than 400 g/mol or a reducing agent that reduces GTN to thionitrate or thionitrite. A preferred GTN converting agent is N-acetylcysteine. Other low mass thiols suitable as GTN converting agents are glutathione, cysteine and cysteinylglycine. A suitable reducing agent is ascorbate including any pharmaceutically acceptable salts of ascorbate including sodium ascorbate as well as ascorbic acid itself (Vitamin C).

Testing to provide a blood concentration of thiol or reducing agent to be used, may be carried out in vitro in blood with GTN dissolved therein at a level of 1 mg/ml to determine concentration of GTN converting agent that effects GTN conversion to thionitrate or thionitrite.

Route of administration for GTN converting agent can be, for example, oral, IV, topical or nebulized.

A preferred dosage and route of administration for N-acetycysteine is IV 7.5-60 mg/kg every six hours or 100 to 600 mg P.O. TID (three times a day).

The polymorphism in the mtALDH gene referred to is the G-to-A polymorphism in exon 12 of the mtALDH gene resulting in a Glu478Lys replacement (glutamic acid is replaced by lysine at position 487) that virtually eliminates mtALDH activity in both heterozygotes and homozygotes and has the highest prevalence in those of East Asian descent. This polymorphism is described in Mackenzie, I. S., et al.

Arterio. Thromb. Vasc. Biol. 25, 1891-1895 (September 2005); Singh, S., Human Genet 83, 119-121 (1989) and Wang, R. S., Drug Metab Dispos. 30, 69-73 (2002). This polymorphism can be tested for by extracting genomic DNA from leukocytes, amplifying the DNA sequence spanning the mtALDH polymorphism by PCR and genotyping by direct sequencing, using an ABI 3100 Sequencer (Applied Biosystems). Alternatively, the polymorphism can be determined by flushing response to ethanol due to marked elevation of blood acetaldehyde which is metabolized by mtALDH from the wild type gene but not from the mutated gene.

The second embodiment herein is directed to treating a patient of East Asian descent who has attenuated response to GTN, i.e., less than 50% of normal metabolism of GTN, usually less than 25% as determined by polymorphism determination as described above.

We turn now to the third embodiment herein. The term "resistant to GTN therapy" is used herein to mean less than 50% of normal metabolism of GTN as determined by having no adequate response to GTN administration, typically less than 25%.

The mtALDH inhibitors which are treating agents include, for example, acetaminophen, chloral hydrate, diadzin, sufonylurea (insulin) and sulfiram. The mtALDH inhibitors effecting resistance to GTN therapy because of ingestion include, for example, ethanol and soy. The mtALDH inhibitors that effect resistance to GTN because of exposure to the inhibitors include, for example, cyanamide and benomyl.

We turn now to the fourth embodiment herein. Consumption of ethanol causes competitive inhibition of mtALDH because its metabolic product acetaldehyde is metabolized by attachment to the same binding site as GTN.

The fourth embodiment is directed to a patient who is an alcoholic and is addicted to and therefore needs or wishes to ingest ethanol, e.g., in beer, wine or alcoholic liquor or liqueur. That patient will be resistant to GTN therapy because the ethanol metabolism product acetaldehyde is competitive with GTN for enzymatic activity of mtALDH. The remedy for this, i.e., to this resistance to GTN therapy, is administering besides GTN, agent that converts GTN to thionitrate and/or thionitrite which is metabolized to nitric oxide or nitric oxide congener without mtALDH activity.

We turn now to the fifth embodiment herein, which is directed to compositions for use in any of the first four embodiments herein.

In one case, the fifth embodiment herein is directed to an oral dosage form, e.g., a pill or capsule for sustained release over 2 to 8 hours, comprising 1 to 10 mg GTN and 100 to 600 mg NAC, e.g., 5 mg GTN and 300 mg NAC (Composition I).

In a second case, the fifth embodiment is directed to an oral dosage form (e.g., tablet or capsule) for sustained release over 2 to 8 hours, comprising 1 to 10 mg GTN and 0.5 to 10 gms ascorbate, e.g., 4 to 10 gms ascorbate, e.g., 5 mg GTN and 4 gms Vitamin C (Composition II).

In a third case, the fifth embodiment is directed to an oral dosage form for sustained release over 2 to 8 hours, comprising 1 to 10 mg GTN and 1 to 500 mg ascorbate, e.g., 5 mg GTN and 500 mg Vitamin C (Composition III).

In a fourth case, the fifth embodiment is directed to an ointment comprising 0.5 to 3% GTN and 5 to 15% NAC, e.g., 2% GTN and 10% NAC (Composition IV).

In a fifth case, the fifth embodiment is directed to a composition for IV administration comprising 5 to 400 mcg/ml NAC, e.g., 50 mg/ml GTN and 75 mg/ml NAC (Composition V).

As used herein, the term ascorbate includes any pharmaceutically acceptable salts of ascorbate including sodium ascorbate as well as ascorbic acid itself (Vitamin C).

The invention is illustrated by the following examples.

EXAMPLE I

A 70-year old patient of Chinese descent has persistent angina. Treatment by infusion with GTN 100 mcg/min has no effect. Infusion of nitroglycerin 100 mcg/min is continued along with infusion of N-acetylcysteine at 50 mg/kg every six hours. After 3 minutes time, the angina is resolved. Alternatively, Composition (V) is administered by infusion and the angina resolves.

EXAMPLE II

An 80-year old patient of Japanese descent has congestive heart failure manifested by pulmonary congestion and low ventricular function. Treatment by infusion with GTN (100 mcg/min) has no effect. Infusion of GTN (100 mcg/min) is continued along with infusion of N-acetylcysteine at 50 mg/kg every 6 hours. After 10 minutes time, pulmonary congestion attenuates and ventricular function improves. Alternatively, Composition V is administered by infusion with the same results.

EXAMPLE III

A 60-year old patient with Type 1 diabetes is on an insulin regimen. The patient develops angina. Sublingual GTN (0.4 mcg) has no effect. Administration of N-acetylcysteine 600 mg P.O. TID or Vitamin C (10,000 mg/day P.O.), along with the sublingual GTN (0.4 mg) causes the angina to resolve. Alternatively, Composition I, II, III or IV is administered with the same results.

EXAMPLE IV

A 70-year old alcoholic needs to imbibe alcohol to avoid withdrawal symptoms. The patient develops angina. Sublingual GTN (0.4 mcg) has no effect. Administration of N-acetylcysteine or glutathione 600 mg P.O. (TID) causes sublingual administration of GTN (0.4 mg) to be effective to cause resolution of the angina. Alternatively, Composition I, II, III, or IV is administered with the same results.

EXAMPLE V

A 60-year old patient of East Asian descent has a heart attack (myocardial infarction). The patient does not respond to IV GTN. The patient is administered Composition V. Coronary pain is relieved.

EXAMPLE VI

A 60-year old alcoholic has restenosis and chest pain. Sublingual GTN at a dosage of 0.5 mg does not relieve chest pain. Supplementation of treatment is carried out with oral NAC (300 mg) or oral vitamin C (10,000 mg/day P.O.) or glutathione 60 mg P.O. (T.I.D.) and chest pain is relieved.

EXAMPLE VII

A 60-year old man of Chinese descent has high blood pressure (200 mmHg systolic). The patient does not respond to 50 mg/min IV GTN. Administration of Composition V (50 mg/ml and NAC 75 mg/ml) at 1 ml/min causes blood pressure to fall to 160 mmHg.

EXAMPLE VIII

A 60-year old alcoholic with obstructive lung disease (chronic obstructive pulmonary disease) has shortness of breath. Conventional treatment does not cause improvement. Nebulized GTN at a dose of 100 micromolar does not cause improvement. Nebulized combination of GTN (dose of 100 micromolar) and NAC (dose of 1 millimolar) causes improvement.

EXAMPLE IX

A 10-year old East Asian patient with asthma experiences shortness of breath. Administration of nebulized combination of GTN (dose of 100 micromolar) and NAC (dose of I millimolar) causes improvement.

EXAMPLE X

A 50-year old Chinese patient with interstitial lung disease (pulmonary fibrosis) experiences shortness of breath despite being on prednisone therapy. Administration of nebulized GTN (dose of 10 micromolar) together with nebulized NAC (dose of 1 millimolar) causes improvement.

EXAMPLE XI

A 50-year old patient with Type 1 diabetes who is on insulin therapy develops recurrent episodes of rectal spasm and associated pain. Administration of Composition IV to the rectal area causes relief of pain.

EXAMPLE XII

A 70-year old Chinese patient experiences a transient ischemic attack. Composition V is administered (50 mg/ml GTN and 75 mg/ml NAC, IV) at 1 ml/min, followed by administration of Composition I. Ischemic stroke does not occur.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method of treating unstable coronary syndrome in a patient in need thereof, wherein there is a loss-of-function in the patient's mitochondrial aldehyde dehydrogenase gene because of a polymorphism in that gene, comprising administering to the patient a therapeutically effective amount of nitroglycerin and an agent which converts nitroglycerin to thionitrate, thionitrite and/or a related nitric oxide cogener which is metabolized without mitochondrial aldehyde dehydrogenase activity, wherein the agent is administered in an amount effective to convert nitroglycerin to thionitrate, thionitrite and/or a related nitric oxide congener which is metabolized without mitochondrial aldehyde dehydrogenase activity.

2. The method of claim 1 wherein the patient needs treatment with nitroglycerin because of angina and the nitroglycerin is administered in an amount effective to reduce precordial discomfort and pressure.

3. The method of claim 1 wherein the patient needs treatment with nitroglycerin because of congestive heart failure and nitroglycerin is administered in an amount effective to reduce pulmonary congestion and increase ventricular function.

4. The method of claim 1 wherein the patient needs treatment with nitroglycerin because of congestive heart failure and nitroglycerin is administered in an amount effective to reduce blood pressure.

5. The method of claim 2 or claim 3 wherein the polymorphism is a loss-of-function mutation in the mitochondrial aldehyde dehydrogenase gene.

6. The method of claim 5 wherein the agent is a thiol of molecular mass less than 400 g/mol.

7. The method of claim 1 wherein the agent is selected from the group consisting of thiols of molecular mass less than 400 g/mol and agents which reduce nitroglycerin to thionitrate and/or thionitrite.

8. The method of claim 7 wherein the agent is selected from the group consisting of N-acetylcysteine, glutathione, cysteine, cysteinylglycine and ascorbate.

9. The method of claim 8 wherein the agent is N-acetylcysteine administered IV in amount of 7.5-60 mg/kg every 6 hours or 100 to 600 mg P.O. TID (by mouth three times a day).

10. The method of claim 1 further comprising the step of determining whether the patient has attenuated response to GTN therapy.

11. The method of claim 1 further comprising the step of determining whether the patient has a polymorphism in the an mtALDH gene.

12. The method of claim 1 further comprising the step of first determining whether the patient is being treated with an mtALDH inhibitor.

13. The method of claim 1 further comprising the step of determining whether the patient has ingested an mtALDH inhibitor.

14. The method of claim 1 further comprising the step of determining whether the patient has been exposed to an mtALDH inhibitor.

15. A method of treating unstable coronary syndrome in a patient in need thereof, wherein there is a loss-of-function in the patient's mitochondrial aldehyde dehydrogenase gene because of a polymorphism in that gene, comprising the determining whether the patient has attenuated response to GTN therapy and if so, then administering to the patient a therapeutically effective amount of nitroglycerin and an agent which converts nitroglycerin to thionitrate, thionitrite and/or a related nitric oxide cogener which is metabolized without mitochondrial aldehyde dehydrogenase activity, wherein the agent is administered in an amount effective to convert nitroglycerin to thionitrate, thionitrite and/or a related nitric oxide congener which is metabolized without mitochondrial aldehyde dehydrogenase activity.

\* \* \* \* \*